United States Patent [19]

Roreger et al.

[11] Patent Number: 6,074,664
[45] Date of Patent: Jun. 13, 2000

[54] MEDICAMENT FORM FOR THE DELIVERY OF COLLAGENASE TO WOUNDS AND PROCESS FOR THE PREPARATION THEREOF

[75] Inventors: Michael Roreger, Neuwied; Heinz Einig, Neustadt, both of Germany

[73] Assignee: Knoll AG, Ludwigshafen, Germany

[21] Appl. No.: 08/875,723

[22] PCT Filed: Jan. 25, 1996

[86] PCT No.: PCT/EP96/00294

§ 371 Date: Nov. 17, 1997

§ 102(e) Date: Nov. 17, 1997

[87] PCT Pub. No.: WO96/23487

PCT Pub. Date: Aug. 8, 1996

[30] Foreign Application Priority Data

Feb. 2, 1995 [DE] Germany ............................ 195 03 338

[51] Int. Cl.⁷ ..................................................... A61L 15/38
[52] U.S. Cl. ............................................. 424/443; 514/953

[58] Field of Search ............................ 424/484, 485–488, 424/443–449; 514/953

[56] References Cited

U.S. PATENT DOCUMENTS 5,206,026   4/1993   Sharik .
5,227,157   7/1993   McGinity et al. .
5,656,286   8/1997   Miranda et al. .

*Primary Examiner*—Edward J. Webman
*Attorney, Agent, or Firm*—Wenderoth, Lind & Ponack, LLP.

[57] ABSTRACT

An administration form for the release of collagenase to wounds is characterised in that it exhibits a combination of specific properties as hereinbelow:

a. it is coherent, flat-shaped and deformable;
b. it has a superficial extension that is equal to or smaller than the wound surface to be treated;
c. it comprises collagenase in defined amounts in homogeneously distributed form;
d. it is designed for the controlled release of collagenase.

13 Claims, No Drawings

6,074,664

MEDICAMENT FORM FOR THE DELIVERY OF COLLAGENASE TO WOUNDS AND PROCESS FOR THE PREPARATION THEREOF

BACKGROUND OF THE INVENTION

In wound treatment, active substances to cleanse the wound and promote healing thereof, for example, the enzyme mixture recovered from the culture filtrate Clostridium histolyticum and consisting of different collagenases, clostripain, and neutral proteases (in the following referred to as collagenase for reasons of simplicity), which must come into direct contact with the bottom of the wound to develop their action. Typically, these wound treatments are administered by means of administration forms which, owing to their consistency, may be applied without interruptions, even to very uneven surfaces. These administration forms include solutions, powders, dusts, and sprays, or semisolid preparations, such as ointments, creams, and gels.

Since the individual dosage is carried out by the user, the main disadvantage of these administration forms lies in the fact that an accurate, reproducible and even dosage of collagenase across the whole application surface is not possible, in particular if the application must be repeated. Moreover, the known administration forms entail further shortcomings. Solutions, powders, dusts, or sprays permit high utilization of the applied collagenase, i.e., the main portion of the administered collagenase takes effect in the wound, but they have the disadvantage that the collagenase can be controlled to an only very limited extent by the administration form. If, for example, a certain collagenase concentration is to be kept constant in the wound over a given period of time, a time-consuming treatment is required involving many quick-releasing single doses to be applied within relatively short intervals. Ointments and creams, however, offer much more possibilities of controlling the collagenase release and of prolonging the action, but, owing to their lipophilla, they have the disadvantage that the collagenase introduced into the wound is utilized to a comparatively small extent because large portions of the collagenase fail to diffuse to the interface to the wound within the application period, so that they cannot be released. With washing the ointment or cream out, this collagenase portion is removed without having taken effect at all.

The use of modern active substance carrier systems and active substance release systems, such as application systems in the form of a patch, which are not introduced into the wound, but are applied on the wound overlapping its edges, is out of the question for collagenase, because this enzyme mixture has a proteolytic action so that it may only get into the wound, but must not reach the wound edge or the intact skin around the wound.

It is accordingly the object of the present invention to find an administration form that has the advantages, but avoids the disadvantages of conventional administration forms in a wound treatment with collagenase, and which makes it possible to release collagenase to the bottom of the wound in an exactly, evenly and reproducibly dosed manner, even in case of repeated application.

Most surprisingly, this object has been found in a deformable, flat-shaped, collagenase-releasing administration form that is characterised by a combination of the following properties:

a. it is coherent, flat-shaped and deformable;
b. it has a superficial extension that is equal to or smaller than the wound surface to be treated;
c. it comprises collagenase in defined amounts in homogeneously distributed form;
d. it is designed for the controlled release of collagenase.

DETAILED DESCRIPTION OF THE INVENTION

According to technical terminology, conventional, deformable, active substance-releasing administration forms, which form flat-shaped structures after application in the wound, such as gels, ointments, creams, or liquid multicomponent systems which react with one another under solidification when joined in the wound, belong to the so-called multiple-dose administration forms. This means that one container comprises a certain quantity of said drug which is designed for a variety of applications involving corresponding dosage procedures. Dosage itself is carried out individually by the user. The user can only give details about the dosed collagenase amount, if he weighs the respective dose prior to application. In case of repeated use, reproducible application of a constant collagenase amount would only be possible with preceding weighing. This individual variable dosage is only possible because of the low coherence and ease of separability of this administration form. On the other hand, said low coherence offers the advantage that the administration form, as mentioned above, can be deformed at will and adapted to uneven surfaces. In contrast, the administration form according to the present invention is a single-dose administration form; similar to tablets or capsules which is coherent and preformed and comprises a defined collagenase dose for one application in homogeneously dispersed form. This has the advantage that the same collagenase amount can be applied as often as desired in a reproducible manner. In this connection, coherence means a strength and internal cohesion of the administration form which, in contrast to the described conventional administration forms, permits handling by the user, wherein handling itself does not automatically determine, change, or influence the predetermined amount of drug and thus the given collagenase amount.

The administration form according to the present invention differs from other single-dose administration forms, for example tablets or capsules, by the fact that it has the coherence required for handling on the one hand, but that it is flexible and deformable on the other hand; after introduction into the wound it can therefore be adapted to the uneven bottom of the wound and brought into contact with it. A precondition for it is that the dimension of the administration is smaller than or at the most equal to the wound surface to be treated. Similar to the mentioned solid administration forms homogeneity of the collagenase distribution is achieved by the fact that a complete mass of the auxiliary agent components is prepared first, and that then collagenase is homogeneously distributed therein.

A variety of divided administration forms having the same shape and weight, therefore all having the same collagenase content, is normally produced from such a mass during the forming process of the administration forms. Typically, a solidification giving the divided, individual administration form its coherence takes place by suitable means as part of the drug forming, e.g., by exerting pressure or by chemical reactions.

To manufacture an administration form according to the present invention, a low-viscous, flowable mass, e.g., a solution, dispersion, or a melt, which comprise collagenase in homogeneously distributed form, is prepared first. This mass is then coated on a sheet-like substrate according to methods known to the skilled artisan. In the production of an administration form according to the present invention the process of hardening, which imparts coherence to the individual separate administration form, does not, in contrast to solid administration forms, take place in the course of forming and dividing the administration forms but prior thereto. The solidification takes place after a plane substrate has been coated, by removing the solvent or dispersion medium by means of drying or, if coating is effected from the melt, by cooling. The kind and strength of cohesive forces building up in this connection depend on the composition of auxiliary agents; this will be explained in more detail hereinbelow. A broad, film-like continuous strip results having a thickness predetermined by the coating. With a given formulation, a limiting factor for the thickness of the strip is the demand for flexibility and deformability of the individual, divided administration form to adapt it to the wound bottom after introduction into a wound. Separating individual administration forms, with a given area from the continuous strip, is effected according to known methods, e.g., by punching or cutting. Since coating is carried out with a mass which comprises the collagenase in homogeneously dispersed form and by observing a constant coat weight, all of the individually separated administration forms comprise the same collagenase quantity in homogeneous distribution. This makes it possible for the user to dose exactly and, in case of repeated application, reproducibly. Since the collagenase content per unit area as well as the surface itself are infinitely variable within wide limits by means of the production method, the administration form according to the present invention offers the opportunity of dosing even very small amounts of collagenase in an accurate and reliable manner. Moreover, the user may dose a collagenase amount which is adapted to the respective problem and therapy requirements. For example, the user may introduce into the wound several administration forms simultaneously and apply them on the bottom of the wound side by side. The user may also separate small pieces from an administration form of given area, for example, when the wound surface to be treated is smaller than the dimension of the administration form, or when the collagenase dose of the administration form, which is given by the area, is too high for a particular treatment. For example, the administration form may be present in combination with an inert, flat-shaped substrate from which it can easily be removed, for example, a siliconized sheet, and be provided with a cm-scale. Since the collagenase charge per unit area of the administration form is known, the user may clip or cut from a lamellar or rolled-up, tape-like administration form the area and consequently the collagenase quantity which he considers necessary from the therapeutic point of view.

In any case, it is possible to shape the superficial extension of the administration form smaller than or, at most, equal to the wound area to be treated. Thus application to the bottom of the wound is possible, and it is ensured that the applied collagenase amount is released in the wound. In an application overlapping the wound edges, only that portion of the administration form extending into the wound would release collagenase, destroying the advantage of accurate dosage.

Another advantage of the administration form according to the present invention is that collagenase may be released in a controlled manner. Since the administration form comes into contact with wound or tissue fluid after application in any case, the interaction with fluid is decisive for the collagenase release, this in turn can be utilized to control the release. For example, the formulation of the administration form according to the present invention may be designed such that the administration form is soluble or decomposable in wound fluid to achieve a relatively rapid release. In this case, the release kinetics for collagenase depends on the dissolution or decomposition rate of the administration form. At the end of the application period, the dissolved or decomposed administration form—similar to ointments and creams—must be washed out of the wound, unless the formulation is designed such that the device is completely decomposable and absorbable in wound exudate.

A delay and prolongation of the collagenase release may be achieved if the composition is chosen such that the administration form only swells under absorption of wound exudate. The wound fluid in particular dissolves the collagenase out of the administration form, resulting in slow erosion thereof. In this case, the collagenase release depends on the swelling capacity and erosion rate of the administration form.

Delaying and prolonging the collagenase release to a still larger extent is achieved if the composition of the administration form is chosen such that it is inert to wound exudate and does not interact with it. In this case, the release kinetics for collagenase only depends on the diffusion rate of collagenase within the administration form and on the interface between device and wound bottom or wound fluid.

In the aforementioned cases where the administration form is not soluble or decomposable, the user has the advantage that he can completely remove it from the wound at any time without having to wash it out or conduct similar manipulations.

According to another preferred embodiment, the administration form according to the present invention has a multilayer structure. For example, a layer which is soluble or decomposable in wound fluid and serves the rapid release of collagenase to achieve the minimum required collagenase concentration as soon as possible, may be joined in the form of a laminate with a swellable or inert layer which serves a slow and uniform release of collagenase to maintain the required collagenase concentration over a longer period.

According to a preferred embodiment of a multilayered administration form, it may be provided with a barrier and/or controlling element not comprising collagenase, for example, a flexible film of polyurethane, polyester, or polypropylene. Such a barrier or controlling element shall guide the collagenase release into a determined direction. If, for example, a deformable, collagenase-releasing layer is applied to the bottom of the wound, a barrier layer laminated thereon may prevent, for example in case of a heavily exudating wound, that collagenase is released to the surrounding wound fluid, which would possibly result in an undesired high dilution effect.

According to another preferred embodiment of the administration form according to the present invention for the treatment of wounds, the device is porous, e.g. like a foam or sponge. The size of the pores and the structure of the administration form are formed such that cells, e.g., fibroblasts, may immigrate into them; thereby the cells are given a structural orientation which is particularly attributable to the degree of order of the sponge structure in the administration form according to the present invention, said degree of order preferably resembling natural connective tissue. The immigration of cells may be necessary, for example, to decompose the preparation, or to release or deposit substances which are required, for example, for tissue regeneration or vascularization of a tissue that is to take the place of the administration form according to the present invention after its decomposition. The preconditions for the administration form's porosity are provided in the course of production, for example, by stirring air into the mass to be coated having collagenase in homogeneous distribution, or by means of external drying conditions which result in the fact that, after coating from a solution or dispersion, the evaporating solvent or dispersion medium leaves holes or pores in the web to be coated.

The selection of materials and auxiliary agents for the production of the administration form according to the present invention is determined first of all by the demands on coherence, flexibility, and deformability, as well as by demands on the desired release kinetics for collagenase. Another limiting factor is that the spectrum of usable materials and auxiliary agents is reduced to those having an excellent tolerance on contact with wound tissue. After application in the wound, the administration form made of a combination of materials and auxiliary agents must not impair the function and activity of cells, such as keratinocytes, fibroblasts, or endothelial cells.

For the manufacture of an administration form according to the present invention, there are at least required auxiliary agents from the group of polymers and auxiliary agents from the group of plasticizers. Polymers ensure the internal cohesion and coherence of the administration form because they form networks after coating and drying or cooling, for example, by means of covalent bonds such as hydrogen bridge bonds or ionic correlations; these networks serve the solidification and therefore provide the required coherence of the administration form. Plasticizers adjust the administration form's consistency such that it is flexible and deformable, and consequently adaptable to the bottom of the wound. Suitable plasticizers with physiological applicability for wound treatment preferably are low-molecular, polyhydric alcohols, for example, glycerol, sorbitol, low-molecular polyethylene glycol, or low-molecular polypropylene glycol.

Water-soluble polymers are particularly suitable for a quick-releasing administration form which is soluble or, at least, decomposable in wound fluid. These preferably include vegetable polysaccharides, such as alginates, pectins, carrageenans, or xanthan; cellulose derivatives, such as methylcellulose, hydroxypropyl cellulose, hydroxyethylcellulose, hydroxypropyl methylcellulose, or sodium carboxymethylcellulose; starch and starch derivatives; galactomannan and galactomannan derivatives; chitosan and chitosan derivatives; glycoproteins, proteoglycans, glucosaminoglycans, polyvinyl alcohol, polyvinyl pyrrolidone, vinyl pyrrolidone-vinyl acetate copolymers, polymolecular polyethylene glycols, and polymolecular polypropylene glycols.

Water-swellable or water-insoluble polymers are particularly suitable for an administration form with a retarded release over a longer period which swells in wound fluid or does not interact with wound liquid. These preferably include cellulose derivatives, such as ethylcellulose, cellulose acetate phthalate, hydroxypropyl methylcellulose phthalate, cellulose acetate succinate, or ethylcellulose succinate, polyoxyethylene-polyoxypropylene-copolymers, polyvinyl alcohol, polyacrylates and polymethacrylates, polylactides, polyglycolides, and polyamino acids.

The administration form may comprise as further auxiliary agents:

preservatives, such as p-Cl-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or, digluconate, ethanol, or propylene glycol, pH-regulators, such as glycerol buffers, citrate buffers, borate buffers, phosphate buffers, or citric acid-phosphate buffers, antioxidants, such as ascorbic acid, ascorbylpalmitate, tocopherol acetate, propyl gallate, butylhydroxyanisole, or butylated hydroxytoluene, auxiliary agents to stabilize the biological activity of active substances, such as mannitol, glucose, lactose, fructose, saccharose, cyclodextrin, or dextran, emusifiable auxiliary agents, such as oils, fats, and waxes, emulsion stabilizers, such as non-ionogenic emulsifiers, amphoteric emulsifiers, cation-active emulsifiers, and anion-active emulsifiers, fillers, such as micro-crystalline cellulose, aluminum oxide, zinc oxide, titanium dioxide, talcum, silicon dioxide, magnesium silicate, magnesium aluminum silicate, kaolin, hydrophobic starch, calcium stearate, or calcium phosphate, foaming agents, such as saponins, alginic acid esters, amine oxides, or fatty amine oxides.

EXAMPLE 1

32 g acetone, 14.6 g ethyl acetate, and 6.5 g polyethylene glycol 400 are placed in a closable mixing vessel. 33.6 g of a polyvinyl pyrrolidone-polyvinyl acetate copolymer, 2 g of a polyoxyethylene-polyoxypropylene copolymer, and 9.3 g hydroxypropyl cellulose are dissolved in this solvent mixture one after the other under even stirring.

Subsequently, a dry-mix of 1 g collagenase (collagenolytic activity 1000 u/g) and 1 g β-cyclodextrin is dispersed in the solution. The homogenous dispersion is spread on a siliconized paper at a weight per unit area of 500 g/m$^2$ and convectively dried in a drying tunnel at 45° C. and an air velocity of about 5 m/sec. After drying, a soft, flexible, transparent film of brownish color is obtained which has a weight per unit area of 267 g/m$^2$ and accordingly an enzyme content of 0.5 mg/cm$^2$ corresponding to a collagenolytic activity of 0.5 units/cm$^2$. Rectangular devices having a surface of 12 cm$^2$ and an enzyme content of 6 mg, corresponding to a collagenolytic activity of 6 units, are cut from this film. Each administration form is placed in a paddle-apparatus and stirred in 50 ml of a 0.01 molar calcium acetate solution at 60 rpm. An excess of a hexapeptide, serving as a substrate for the enzymatic decomposition by collagenase, is added to the solution. After 5 minutes, a sample of the solution is taken, and an excess of ninhydrine is added which forms with the tripeptides, resulting through the enzymatic decomposition of the hexapeptide substrate, a color complex which is measured spectrophotometrically and shows an enzymatic activity of 6.36 units.

Thus collagenase is released to the extent of 100% after only 5 minutes. The desired demand on the flexible film in the chosen composition, i.e., to achieve in the wound the highest possible enzyme concentration within the shortest possible time can therefore be met.

EXAMPLE 2

32 g acetone, 14.7 g ethyl acetate, and 6.5 g polyethylene glycol 400 are placed in a closable mixing vessel. 33.1 g of a polyvinyl pyrrolidone-polyvinyl acetate copolymer, 1.9 g of a polyoxyethylene-polyoxypropylene copolymer, and 9.3 g hydroxypropyl cellulose are dissolved in this solvent mixture one after the other under even stirring. Subsequently, a dry-mix of 1 g collagenase (collagenolytic activity 1000 u/g), 1 g Dextran 40, and 0.5 g calcium acetate is dispersed in the solution. The homogenous dispersion is spread on a siliconized paper at a weight per unit area of 500 g/m$^2$ and convectively dried in a drying tunnel at 45° C. and an air velocity of about 5 m/sec. After drying, a soft, flexible, transparent film of brownish color is obtained which has a weight per unit area of 266.5 g/m$^2$ and accordingly an enzyme content of 0.5 mg/cm$^2$ corresponding to a collagenolytic activity of 0.5 units/cm$^2$. Rectangular administration forms having a surface of 1 2 cm$^2$ and an enzyme content of 6 mg, corresponding to a collagenolytic activity of 6 units, are cut from the film. Each administration form is placed in a paddle-apparatus and stirred in 50 ml of a 0.01 molar calcium acetate solution at 60 rpm. An excess of a hexapeptide, serving as a substrate for the enzymatic decomposition by collagenase, is added to the solution. After 5 minutes, a sample of the solution is taken, and an excess of ninhydrine is added which forms with the tripeptides, resulting through the enzymatic decomposition of the hexapeptide substrate, a color complex which is measured spectrophotometrically and shows as the result a collagenolytic activity of 5.52 units.

Thus collagenase is released to the extent of more than 90% after only 5 minutes. The desired demand on the flexible film in the chosen composition with dextran and calcium acetate to stabilize the collagenase activity, i.e., to achieve in the wound the highest possible collagenase concentration within the shortest possible time can therefore be met.

EXAMPLE 3

It is desired to obtain a flexible film which—in contrast to the films according to Examples 1 and 2—has a retarded release. 40 g acetone, 20 g ethyl acetate, and 7 g polyethylene glycol 400 are placed in a closable mixing vessel. 15 g of a polyvinyl pyrrolidone-polyvinyl acetate copolymer, 1.2 g of a polyoxyethylene-polyoxypropylene copolymer, 6.5 g hydroxypropyl cellulose, and 8.3 g ethylcellulose are dissolved in this solvent mixture one after the other under even stirring.

Subsequently, a dry-mix of 1 g collagenase (collagenolytic activity 1000 u/g) and 1 g β-cyclodextrin is-dispersed in the solution. The homogenous dispersion is spread on a siliconized paper at a weight per unit area of 500 g/m$^2$ and convectively dried in a drying tunnel at 45° C. and an air velocity of about 5 m/sec. After drying, a soft, flexible, transparent film of brownish color is obtained which has a weight per unit area of 200 g/m$^2$ and accordingly an enzyme content of 0.5 mg/cm$^2$ corresponding to a collagenolytic activity of 0.5 units/cm$^2$. Rectangular administration forms having an area of 12 cm$^2$ and an enzyme content of 6 mg, which corresponds to a collagenolytic activity of 6 units, are cut from this film. Each device is placed in a paddle-apparatus and stirred in 50 ml of a 0.01 molar calcium acetate solution at 60 rpm. An excess of a hexapeptide, serving as a substrate for the enzymatic decomposition by collagenase, is added to the solution. After 5 and 60 minutes, a sample of the solution is taken, and an excess of ninhydrine is added which forms with the tripeptides, resulting through the enzymatic decomposition of the hexapeptide substrate, a color complex which is measured spectrophotometrically and shows an enzymatic activity of 5.64 units after 30 minutes.

After 5 minutes, collagenase has been released to a considerably lesser extent as compared to Examples 1 or 2, and not before 60 minutes the release exceeds 90%.

The desired demand on the flexible film in the composition with the addition of ethylcellulose, i.e., to achieve a comparatively retarded release of collagenase over at least 60 minutes can therefore be met.

EXAMPLE 4

It is desired to obtain a flexible film which, in contrast to the three previous examples, may be prepared without the use of organic solvents, and has a very quick release.

67.75 polyethylene glycol 1500 are molten together with 6.0 g polyethylene glycol 400 at a temperature of 90° C. in a glass vessel while stirring. 20.0 g of a polyvinyl pyrrolidone/vinyl acetate copolymer are dissolved in this melt under stirring, at 90° C. After cooling of the melt to 45° C., 6.25% of a mixture of collagenase, dextrane 40 and calcium acetate (mass ratio 2:2:1, activity of the collagenase 1000 U/g) is added in portions to the mass and is dispersed by stirring. The homogeneous mass is subsequently spread onto a PETP-sheet to form a film having the weight per unit area of 400 g/m$^2$. After cooling, a soft, flexible and substantially transparent film of brownish colour is obtained having a collagenolytic activity of 1 U/cm$^2$. After covering with a second PETP-sheet rectangular administration forms with rounded corners and surfaces of 25 cm$^2$, corresponding to 25 U collagenase, are punched out of this film.

The administration forms dissolve completely in physiological sodium chloride solution within 5 minutes, releasing in the process the active substance collagenase at 100%. Thus they meet the requirement of being able to release large amounts of the active substance at the application site within a very short period of time. Moreover, this method of manufacture obviates the problem of drying solvent residues out of the film.

EXAMPLE 5

It is desired to obtain a film which, as in Example 4, is manufactured without using organic solvents, but which has a considerably retarded release and is insoluble in aqueous media.

At 120° C., 27.0 g Vaseline are molten with 15.0 g middle-chain triglycerides. In this melt 20.0 g poloxamer, 10.0 g cetylstearyl alcohol and 20.0 g of an ethyl acetate/vinyl acetate copolymer are molten or dissolved, respectively—one after the other and under stirring. The clear and homogeneous mass is cooled down to 45° C. while stirring. To the cooled mass there are then added, one after the other, 1,75 g of a mixture of dextrane 40 and calcium acetate (mass ratio 2:1), and 6.25 g of a mixture of collagenase, dextrane 40 and calcium acetate (mass ratio 2:2:1, activity of the collagenase 1000 U/g). This batch is stirred until a macroscopically homogenous distribution is obtained.

Subsequently the mass is spread onto a PETP-sheet to form a film having a weight per unit area of 400 g/m$^2$. After cooling, a soft very flexible, slightly opaque film of brownish colour is obtained which has a collagenolytic activity of 1 U/cm$^2$. After covering with a second PETP-sheet, rectangular administration forms having rounded corners and surfaces of 25 cm$^2$, corresponding to 25 U collagenase, are punched out of this film.

The administration forms are insoluble in physiological sodium chloride solution. They release the active substance collagenase continuously over a period of 24 h, during which process they gradually lose their colour. When the active substance has been completely released, the administration forms, which have meanwhile become white, can be removed again from the test solution in one piece. Thus they meet the requirements (1) of continuously releasing active substance over a prolonged period of time and (2) being capable of being removed from the application site without washing them out or other manipulations.

What is claimed is:

1. A foil or flat-shaped pharmaceutical composition for the controlled release of collagenase to a wound, wherein the composition:
   (a) is coherent and sufficiently flexible to conform to uneven wound surfaces,
   (b) contains collagenase in an area-specific concentration,
   (c) is adaptable to the wound such that the composition does not extend beyond the border of the wound surface,
   (d) comprises collagenase in a defined amount which is homogeneously distributed throughout the composition,
   (e) allows for the controlled release of collagenase to said wound, and
   (f) comprises at least one polymer influencing the rate of release and at least one plasticizer as auxiliary agents.

2. The pharmaceutical composition according to claim 1, which consists of several parts which can be introduced in a wound in several small pieces.

3. The pharmaceutical composition according to claim 1, which is undivided and, in order to not extend beyond the border of the wound surface, can individually be cut to the area of the wound prior to application.

4. The pharmaceutical composition according to claim 1, which is soluble or decomposable in wound fluid, the release kinetics for collagenase depends on the dissolution or decomposition rate of the composition.

5. The pharmaceutical composition according to claim 1, which is degradable and absorbable in wound fluid.

6. The pharmaceutical composition according to claim 1, which is swellable in wound fluid, the release kinetics for collagenase depending on its erosion rate.

7. The pharmaceutical composition according to claim 1, which is inert to the wound exudate, the release kinetics for collagenase only depends on the diffusion rate of collagenase within the pharmaceutical composition and on the interface between device and application site or wound fluid, respectively.

8. The pharmaceutical composition according to claim 1, having a multilayered structure.

9. The pharmaceutical composition according to claim 8, comprising at least one barrier and/or controlling element to guide the collagenase release in a certain direction.

10. The pharmaceutical composition according to claim 1, wherein said polymer is a water-soluble polymer.

11. The pharmaceutical composition according to claim 1, wherein said polymer is a water-swellable polymer and/or water-insoluble polymer.

12. A pharmaceutical composition in the form of a film for the controlled release of collagenase to a wound, wherein the composition:
   (a) is coherent and sufficiently flexible to conform to uneven wound surfaces,
   (b) contains collagenase in an area-specific concentration,
   (c) is adaptable to the wound such that the film does not extend beyond the border of the wound surface,
   (d) comprises collagenase in a defined amount which is homogeneously distributed through the composition,
   (e) allows for the controlled release of collagenase to said wound, and
   (f) comprises at least one polymer influencing the rate of release and at least one plasticizer as auxiliary agents.

13. A process for producing an administration form for the release of collagenase to a wound, said process comprising:
   preparing a low viscous, flowable mass, solution, dispersion or melt, which comprises collagenase in a homogeneously distributed form, and at least one polymer influencing the rate of release and at least one plasticizer as auxiliary agents;
   coating the flowable mass, solution, dispersion or melt onto a sheet-like substrate;
   drying the mass, solution, dispersion by removing the solvent or dispersion medium or, in the case of the melt, by cooling the melt, to form a film-like sheet material having a thickness of the coating; and
   separating a number of administration forms of the same shape and same weight from the film-like sheet.

* * * * *